United States Patent [19]

Russo

[11] Patent Number: 5,676,136
[45] Date of Patent: Oct. 14, 1997

[54] PROTECTIVE SUCTION CONTROL CATHETER WITH VALVE

[76] Inventor: Ronald D. Russo, 8 Candleberry Rd., Barrington, R.I. 02806

[21] Appl. No.: 438,850

[22] Filed: May 11, 1995

Related U.S. Application Data

[63] Continuation of Ser. No. 163,282, Dec. 7, 1993, abandoned.

[51] Int. Cl.$^6$ .............................. A62B 9/02; A61M 5/00
[52] U.S. Cl. .................. 128/205.24; 128/205.12; 128/207.14; 128/207.16; 604/902; 604/119
[58] Field of Search .................... 604/119, 902, 604/163, 171, 192, 263, 267; 128/205.12, 205.19, 205.24, 207.14, 207.16, 911, 912, 909, DIG. 26

[56] References Cited

U.S. PATENT DOCUMENTS

| | | |
|---|---|---|
| 2,674,262 | 4/1954 | Bradshaw . |
| 3,319,628 | 5/1967 | Halligan ............................ 604/119 |
| 3,547,147 | 12/1970 | Shay . |
| 3,595,234 | 7/1971 | Jackson .......................... 604/119 |
| 3,834,388 | 9/1974 | Saver ............................ 604/119 |
| 3,937,220 | 2/1976 | Coyne . |
| 3,991,762 | 11/1976 | Radford ...................... 128/207.14 |
| 4,062,363 | 12/1977 | Bonner . |
| 4,193,406 | 3/1980 | Jinotti ......................... 128/205.24 |
| 4,287,889 | 9/1981 | Stupar ............................ 604/119 |
| 4,356,823 | 11/1982 | Jackson . |
| 4,420,101 | 12/1983 | O'Neill . |
| 4,534,542 | 8/1985 | Russo ............................ 604/902 |
| 4,569,344 | 2/1986 | Palmer ....................... 128/207.16 |
| 4,634,433 | 1/1987 | Osborne . |
| 4,638,539 | 1/1987 | Palmer . |
| 4,792,327 | 12/1988 | Swartz ........................... 604/902 |
| 4,825,859 | 5/1989 | Lambert ..................... 128/207.14 |
| 4,834,726 | 5/1989 | Lambert ..................... 128/207.14 |
| 4,925,450 | 5/1990 | Imonti et al. .................. 604/902 |
| 4,967,743 | 11/1990 | Lambert . |
| 5,083,561 | 1/1992 | Russo . |
| 5,088,486 | 2/1992 | Jinotti ........................ 128/207.14 |
| 5,139,018 | 8/1992 | Brodsky et al. ............... 128/207.14 |
| 5,215,522 | 6/1993 | Page et al. . |

OTHER PUBLICATIONS

Superior Plastic Products Corp. brochure published 1984 showing use of Russo (Rey. E.) device.

Primary Examiner—Kimberly L. Asher
Attorney, Agent, or Firm—Robert J. Doherty

[57] ABSTRACT

A sterile suction catheter protecting both the user and patient from cross contamination. The catheter enclosed in a protective and collapsible sleeve along with a closed capped suction control valve. The sleeve and cap preserving the sterility of the catheter assembly while protecting the user from contact with potentially infectious aspirated secretions. Both sleeve and cap readily and easily assembled on the catheter to minimize labor and to reduce cost to make the assembly inexpensive. For single procedure use and disposable after termination of the suction procedure.

15 Claims, 3 Drawing Sheets

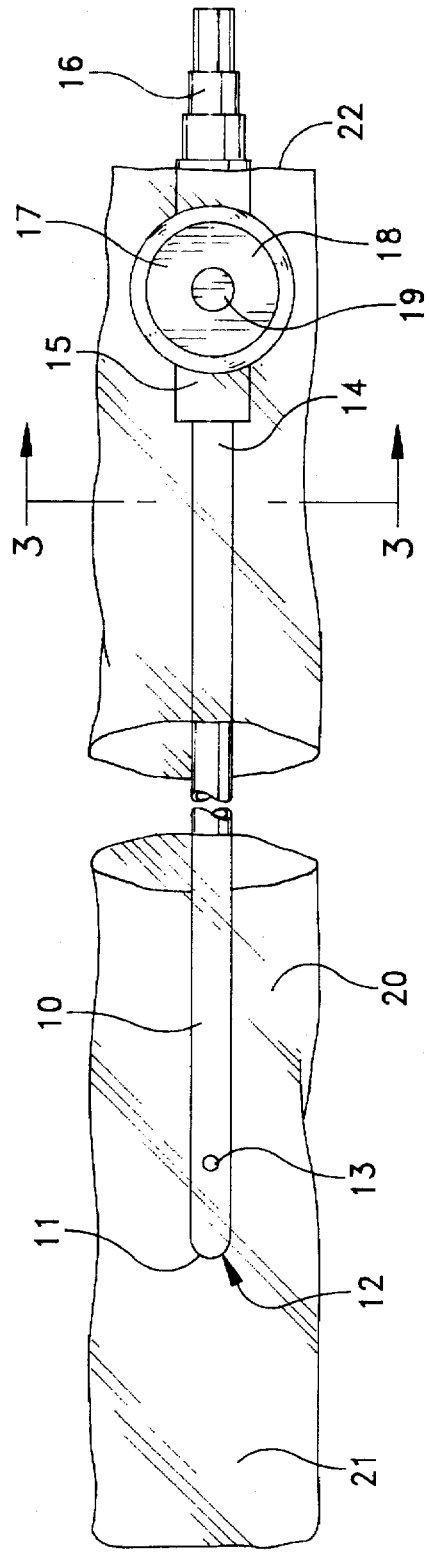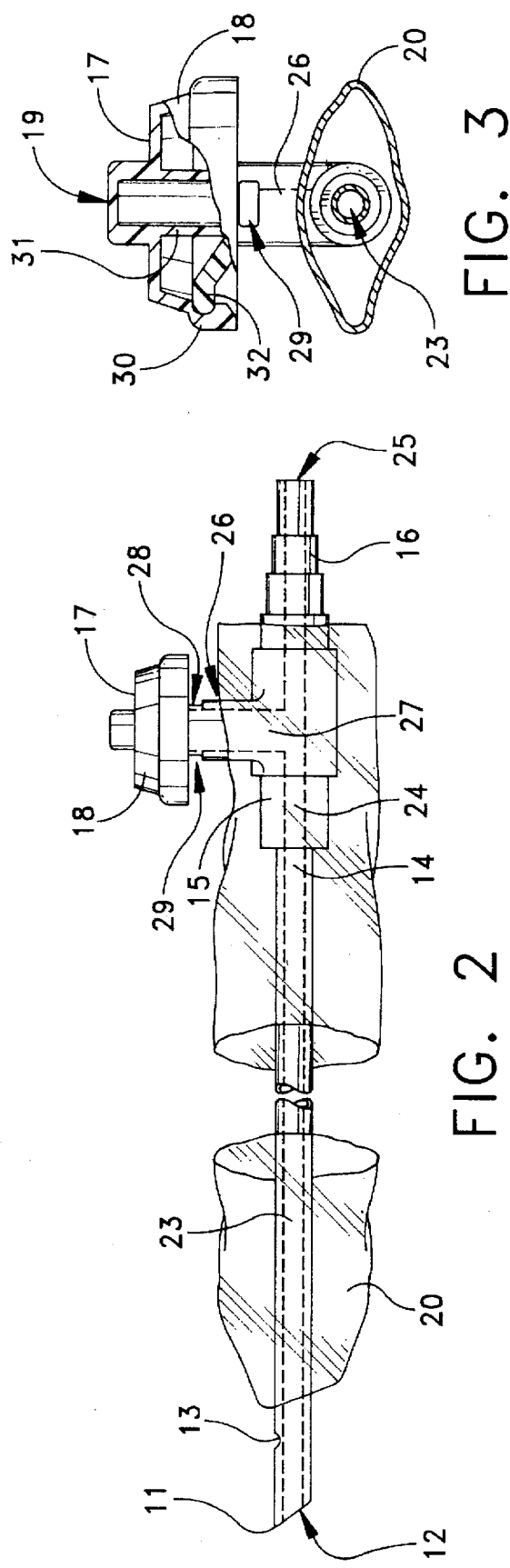

PROTECTIVE SUCTION CONTROL CATHETER WITH VALVE

This application is a continuation of application Ser. No. 08/163,282, filed Dec. 7, 1993, now abandoned.

BACKGROUND OF THE INVENTION

Sterile disposable suction catheters are widely used for removing fluids from the tracheal and bronchial passages of patients. Patients who are intubated with an endotracheal tube are often connected to a respirator and these types of patients typically require frequent suctioning about once every hour or so.

Respirator patients who require this frequent suctioning use the latest closed tracheal suction devices such as Palmer U.S. Pat. No. 4,638,539, Lambert U.S. Pat. No. 4,967,743, or Russo U.S. Pat. No. 5,083,561. These type of closed tracheal suction devices remain directly attached or coupled to the endotracheal tube and respirator circuit and the same catheter is used repeatedly for suctioning. For these respirator patients, the above devices are ideal, although they are expensive.

There are many patients, however, who are not connected to a respirator who require less frequent suctioning to clear a tracheostomy tube, or the mouth, or nasal passages. For these patients, a sterile disposable plastic type inexpensive suction catheter is often used. They are used once and then discarded. Unlike the closed tracheal devices which totally protect the user from contacting potentially infectious secretions, the single use catheters typically do not.

With some success, several attempts have been made to improve the single use catheters. Coyne U.S. Pat. No. 3,937,220 shows a sleeved single use suction catheter with a completely open type suction control valve. Russo in U.S. Pat. No. 4,534,542 shows a partially closed suction control valve with a cap that has a series of vent holes.

The sleeve on the Coyne U.S. Pat. No. 3,937,220 does protect the catheter and user from contamination. However, the open type suction control valve gives no protection to the user's thumb during use. In addition, the sleeve of Coyne requires a considerable amount of labor to attach to the catheter and the banding method used is very tedious and expensive. Because of this the sleeved catheter of Coyne presently costs the hospital about $1.80 each while an unsleeved single use disposable nonsleeved catheter costs only about $0.60.

The additional prior art sleeved catheters of Bonner U.S. Pat. No. 4,062,363 and Osborne U.S. Pat. No. 4,634,433 also show labor intensive o-rings or bands and are more expensive than Coyne.

Russo's suction control valve in U.S. Pat. No. 4,534,542 does afford some protection to the user's thumb, however some users feel that the holes in the cap of the valve are potential leak paths for bacteria or viruses to directly contact the thumb.

Most recently Page et. al. U.S. Pat. No. 5,215,522 references much of the prior art and shows a single use sleeved catheter with a normally closed suction control valve which is more contamination resistant than the normally open suction control valve of Russo U.S. Pat. No. 4,532,542.

However, the valve structure of Page et. al. U.S. Pat. No. 5,215,522 is a more complicated three piece assembly requiring a separate retainer to hold the resilient valve in place compared to the simpler and much less costly two piece assembly of Russo U.S. Pat. No. 4,532,542. Page et. al. also uses the labor intensive collar structure to assemble the sleeve to the valve.

Due to the complexity and cost associated with the Page et. al. device, it is better suited to a reusable closed type system than a single use disposable catheter device.

Because of these limitations and the excessive costs of the single use sleeved catheters, most hospitals still purchase disposable catheter kits that include sterile packaged latex gloves and drapes and do not have sleeves.

BRIEF SUMMARY AND OBJECTS OF THE INVENTION

With the foregoing in mind, the present invention offers a totally enclosed sterile single use disposable suction catheter that offers maximum user protection against contact with aspirated secretions at the same cost as presently used non-protected disposable suction catheters.

The present invention, among other things, is a sleeved catheter with a closed cap suction control valve which protects both hands of the user while making the suctioning procedure less cumbersome and less expensive for the hospital. Accordingly, it is a primary object to provide an easy to use, less complicated, single patient use device which provides the utmost protection to the user from aspirated secretion contact.

An object of the invention is to provide a sterile suction catheter which maintains its sterility during preparation and set up to prevent the catheter from contacting any foreign object.

It is another objective of the invention to provide a sterile suction catheter which is easy to handle and use without contaminating the catheter.

It is another objective of the invention to provide a suction catheter which saves time during set up and requires no special teaching or learning procedures to use.

It is another object to provide a catheter with a closed capped suction control valve which can apply either continuous or intermittent suction, prevents splash back of secretions out the valve, and prevents the user's thumb from contacting aspirated secretions.

Another object is to reduce the number of additional supplies needed and to thus lower the cost of the suction procedure because sterile wrapped gloves and drapes are not needed to use the catheter.

Another object of the invention is to create less mess and clean up after use.

Another object is to create an easy, fast, inexpensive to assemble catheter including a sleeve and a closed capped suction control valve.

DETAILED DESCRIPTION OF THE ILLUSTRATED EMBODIMENT

FIG. 1 is a top view of the catheter assembly.

FIG. 2 is a side view of the catheter assembly of FIG. 1 wherein the protective sleeve is illustrated in a retracted position with the catheter tube extended for insertion into a patient.

FIG. 3 is a partial cross sectional view of the catheter assembly taken along lines 3—3 in FIG. 1.

Figure 4:
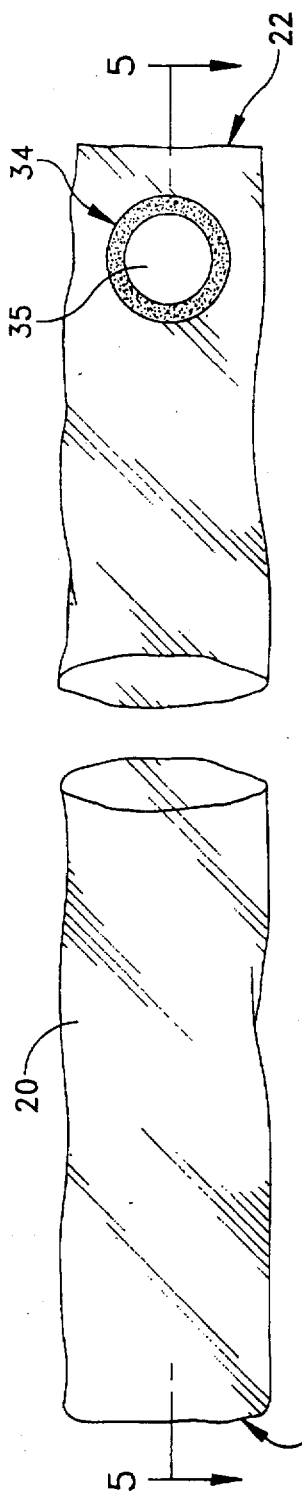
FIG. 4 is a top view of the sleeve showing the valve insertion through hole.

FIG. 1 is a top view of the catheter assembly showing flexible catheter 10 typically extruded from PVC plastic. The front or distal end 11 is rounded smooth with an opening 12 and a side eye 13.

The rear or proximal end of the catheter 14 is attached to injection molded rigid PVC valve body 15 by solvent cement. The valve body 15 includes a stepped connector portion 16 and a separately injection molded valve cap 17 is snapped onto the valve body 15. The valve cap 17 is molded from a resilient synthetic rubber santoprene of about 70 shore durometer made by Monsanto plastics.

As can be seen, the valve cap 17 is molded with a closed dome shaped cover 18 and a molded in depression button portion 19.

Enclosing the catheter is a tubular flat polyethylene sleeve 20 which extends beyond the distal tip of the catheter in portion at least about 2 inches.

The sleeve forms a protective envelope around the full length of the catheter and extends rearward to cover the valve body 15 and ends at 22 just leaving the connector 16 to be not covered by sleeve 20.

FIG. 2 shows a side view of the assembly with the sleeve 20 in a collapsed retracted position and the distal end 11 of the catheter ready to be inserted into a patient.

The catheter lumen 23 extends the full length of the catheter and continues into a matching internal lumen 24 in valve body 15 and exits out the valve body at connector lumen 25.

As such, a continuous suction lumen extends from distal tip 12 and terminates at connector lumen 25.

The valve body 15 includes a side-stem section 26 with a bypass passageway 27. The stem section also has two vent slots 28 and 29 which are molded in as part of the stem 26 and open the bypass passageway 27 to atmosphere.

Valve cap 17 completely closes off the bypass passageway such that the slots 28 and 29 are the only exit openings on the stem 26 to atmosphere.

FIG. 3 is a cross sectional view showing the stem 26 and cap 17 in greater detail. One of the vent slots 29 is clearly depicted. Cap 17 snaps over a rim 32 at undercut groove 30 on cap 17. Internal to cap 17 is molded in plunger seal 31 which acts to effectively move downward to seal off vent slots 28 and 29 when button 19 is depressed.

FIG. 4 shows the tubular lay flat polyethylene film extruded sleeve which has a typical wall thickness of about 1½ mils. making it a flexible, collapsible yet very strong film tube.

The distal end of the sleeve 33 is preferably open so the catheter can easily move out the end of the sleeve 33 when in use. However, the assembly can be produced with the end 33 sealed closed with a perforated tear seal to maintain sterility. The tear seal can be easily stripped off by the user just before use to open end 33 if desired.

Sleeve end 22 is always open. During manufacture the tubular sleeve 20 has a ¾ inch diameter circle 34 printed as part of the sleeve and located just inboard of sleeve end 22. Because the sleeve is clear the circle is printed in a contrasting color such as dark blue or black.

A through hole 35 is punched through the sleeve on center with circle 34.

Figure 5:
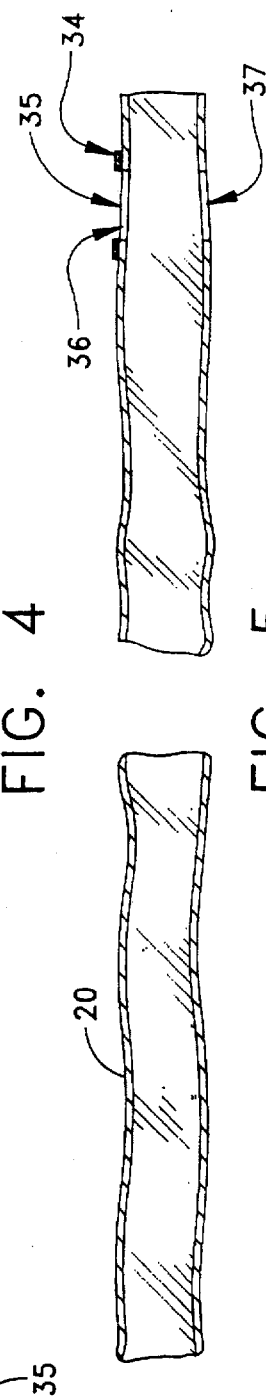
FIG. 5 is a cross sectional view of the sleeve taken along lines 5—5 in FIG. 4.

FIG. 5 is a side-view of the sleeve clearly showing through hole 35 punched through both walls 36 and 37 on the sleeve.

The through hole is 0.350 inches in diameter which is the same diameter as stem 26 on valve body 15.

The dark printed circle 34 serves as an easy to locate visual guide for through hole 35.

Figure 6:
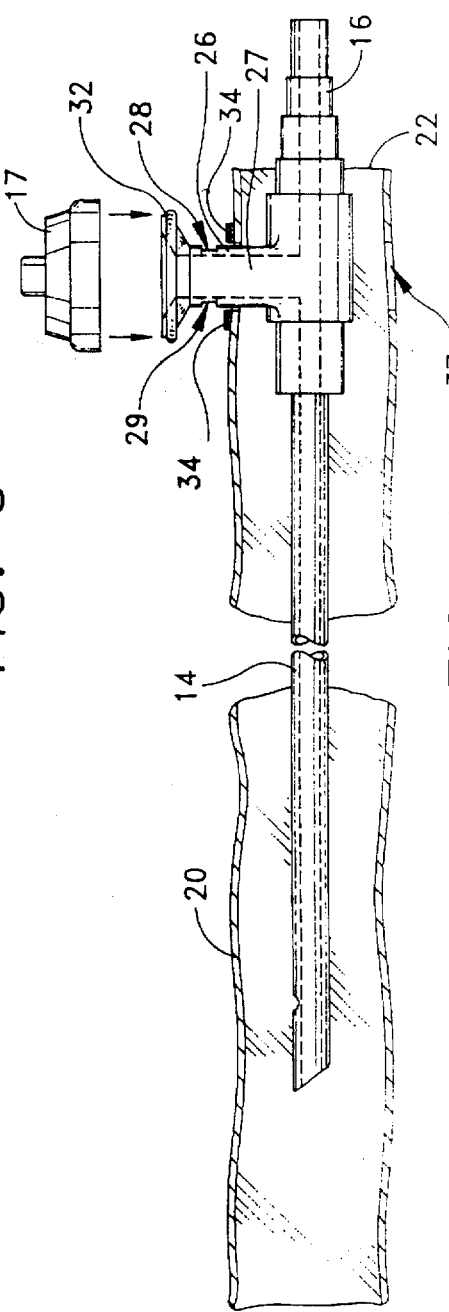
FIG. 6 is a side view of the catheter assembly showing the valve body inserted into the through hole.

FIG. 6 is a side view of the assembly showing the catheter with valve body 15 inserted into sleeve 20. The sleeve 20 is about 2 inches wide which fully accepts the catheter with valve body to be completely inserted into the sleeve.

Through hole 35 is slightly stretched over rim 32 on the valve body 15 so that it fits snuggly around stem 26.

Once cap 17 is snapped down over rim 32 the sleeve is then captured such that it cannot become disengaged from the stem 26.

Dark circle 34 aids the assembler in easily locating the hole 35 to make the sleeve to catheter assembly fast and easy and inexpensive.

No separate band or o-ring is needed and manual handling of the sleeve is kept to a minimum to reduce labor cost.

Once the valve cap 17 is in place, such along with the sleeve 20 essentially completely encloses the assembly. The connector 16, however, is left extending out sleeve end 22 ready for connection to suction tubing and to a source of suction which is readily available in the patient's room. The assembly is also open to the outside at the hole 35 through wall 37.

Figure 7:
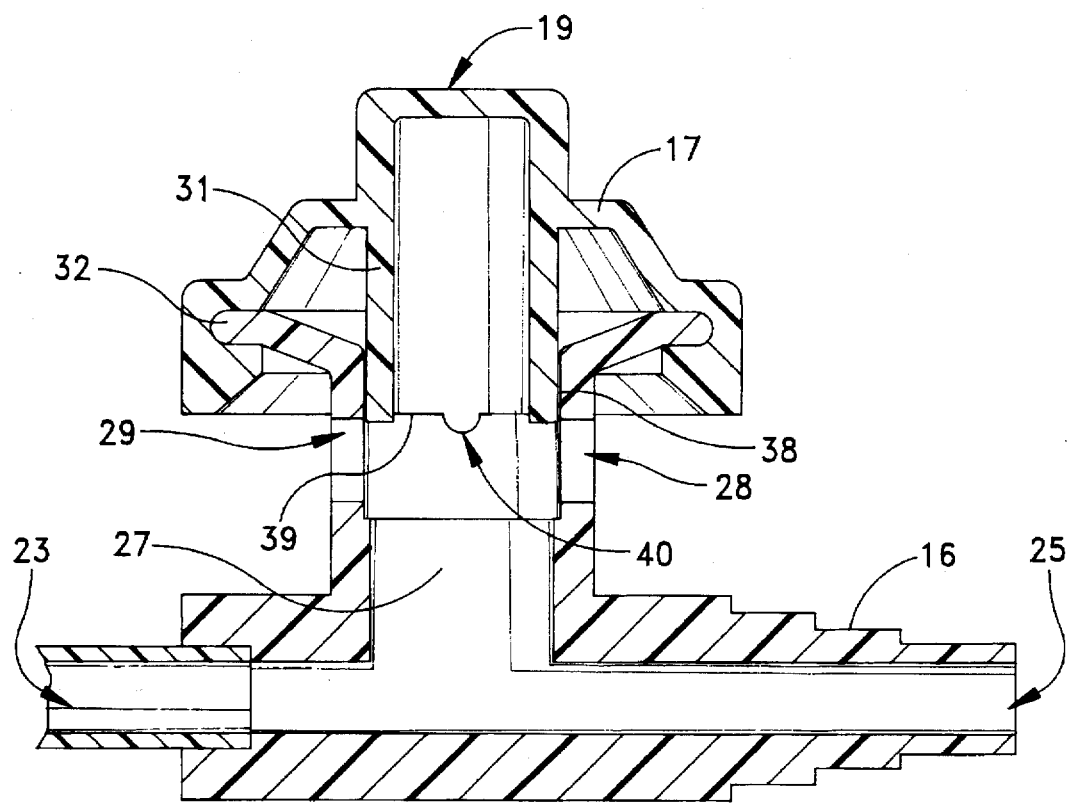
FIG. 7 is a partial cross-sectional view of the suction control valve in its normally open non-suction applied to the catheter position.

FIG. 7 is a cross-sectional view of the suction control valve in its normally open non-activated position. Valve cap 17 which has plunger seal 31 is fitted closely inside side-wall 38 within bypass passageway 27. On the underside of plunger seal 31 is sealing ring 39 which includes several raised dimples 40.

In FIG. 7 the sealing ring 39 is shown in its upward position above vent slots 28 and 29. In operation, when suction is applied to connector lumen 25 vented atmosphere is aspirated through open slots 28 and 29 through passageway 27 and out through connector lumen 25. The catheter lumen is completely bypassed such that no suction is applied to catheter lumen 23 when the valve is in its normally open position as depicted in FIG. 7.

Figure 8:
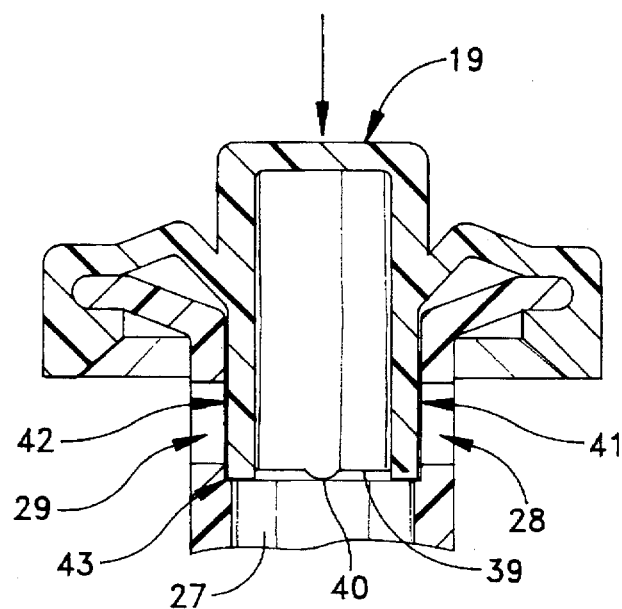
FIG. 8 is a partial cross-sectional view of the suction control valve in its depressed closed suction applied to the catheter position.

FIG. 8 shows the resilient valve cap 17 in its depressed closed position wherein plunger seal 31 moves downward such that vent slots 28 and 29 are closed by plunger side-walls 41 and 42. Sealing ring 39 along with raised dimples 40 are slightly compressed on seat 43 to seal off bypass passageway 27 thus applying all the suction to the catheter lumen.

The raised dimples 40 serve as a vacuum break to instantaneously unseat the sealing ring to permit the valve cap to immediately return to its normally open position when thumb pressure is removed from button 19.

As can be seen, all the suction and aspirated secretions remain within the valve body below seat 43. The operator's thumb is kept completely dry and away from any contact with aspirated secretions within the valve.

Suction can be applied to the catheter continuously by leaving the valve cap continuously depressed or intermittently by on and off depression of the button 19.

The entire catheter assembly consists of four inexpensive components: The catheter, the sleeve, valve body, and valve cap which are assembled quickly and inexpensively with a minimum amount of labor and assembly time.

The invention produces an inexpensive sterile suction catheter which effectively protects both the user and patient from cross contamination. It eliminates the need for expensive latex sterile gloves and is very cost effective when compared with the standard single use catheters presently used.

While the suction control valve is used in conjuction with a suction catheter it could also be used as part of other suction instruments such as bronchial aspirators or surgical suction instruments.

While there is shown and described one particular embodiment of the catheter assembly, it will be apparent to anyone skilled in the art to make various modifications without departing from the spirit and scope of the underlying inventive concept and that the invention is not limited to the particular forms herein shown. For instance, different french size catheters can be employed with many different types of suction tips such as DeLee type or whistle tip. The position and type of slots or holes can be located anywhere on the valve body and the connector could be tapered, smooth, or stepped as preferred.

What is claimed:

1. A sterile suction catheter assembly normally open to atmosphere comprising a flexible tube and a suction control regulator in suction communication with each other, said regulator having a main body with a suction lumen extending therethrough and in turn terminating at one end thereof with said flexible tube and at the other end with a connector for applying suction to said assembly and a bypass stem having a stem body wall transversely extending outwardly from said main body and terminating in an open outer end having a peripheral rim and in turn including a vent passage which extends from said suction lumen outwardly to said open outer end, said flexible tube, said suction lumen and said connector all open and unobstructed with no means therein for blocking passage of gases therethrough during operation of the catheter assembly in either the non suction position or the suction applying position thereof, said stem body wall including at least one vent hole open to atmosphere and disposed at a point inwardly spaced from said outer end peripheral rim, a valve closure cap having a completely imperforate outer surface positioned on said outer end peripheral rim and closing said vent passage except for said vent hole, said cap outer surface of a lateral extent substantially greater than that of said stem body wall and overlaying said vent hole, said vent hole being shielded by said cap outer surface, said cap being normally biased to a non-suction applied open position wherein the vent hole remains open to atmosphere, and said cap being resiliently manually inwardly depressable to a suction applied closed position wherein said vent hole is obstructed to seal off the vent passage to a closed to atmosphere position.

2. A sterile suction catheter assembly normally open to atmosphere comprising a flexible tube and a suction control regulator in suction communication with each other, said regulator having a main body with a suction lumen extending therethrough and in turn terminating at one end thereof with said flexible tube and at the other end with a connector for applying suction to said assembly and a bypass stem having a stem body wall transversely extending from said main body and terminating in an open outer end and in turn including a vent passage which extends from said suction lumen to said open outer end, said flexible tube, said suction lumen and said connector all open and unobstructed with no means therein for blocking passage of gases therethrough during operation of the catheter assembly in either the non suction position or the suction applying position thereof, said stem body wall including at least one vent hole open to atmosphere and disposed at a point inwardly spaced from said outer end, a completely closed valve closure cap positioned on said outer end and closing said passageway except for said vent hole, said cap being normally biased to a non-suction applied open position wherein the vent hole remains open to atmosphere, and said cap being resiliently manually depressable to a suction applied closed position wherein said vent hole is obstructed to a closed to atmosphere position to seal off the passage to directly apply suction to the flexible tube, said stem body wall being cylindrical and said cap including an inwardly extending tubular plunger having an outer cylindrical wall adapted to move inwardly and outwardly within said stem body wall from the normally open to atmosphere position where said plunger wall is disposed outwardly of said vent hole to a closed to atmosphere position where said plunger wall extends across at least portions of said vent hole.

3. The catheter assembly of claim 2, said regulator main body being rigid and said closure cap being resilient.

4. The catheter assembly of claim 2, said valve closure cap having an outer surface wall hand engageable by the operator of the device and of a lateral extent substantially greater than that of said stem body wall, said vent hole being shielded by said outer surface.

5. A sterile suction catheter assembly normally open to atmosphere comprising a flexible tube and a suction control regulator in suction communication with each other, said regulator having a main body with a suction lumen extending therethrough and in turn terminating at one end thereof with said flexible tube and at the other end with a connector for applying suction to said assembly and a bypass stem having a stem body wall transversely extending from said main body and terminating in an open outer end and in turn including a vent passage which extends from said suction lumen to said open outer end, said stem body wall including at least one vent hole open to atmosphere and disposed at a point inwardly spaced from said outer end, a completely closed valve closure cap positioned on said outer end so as to close said passageway except for said vent hole, said cap having normally biased to a non-suction applied open position wherein the vent hole remains open to atmosphere, and said cap being resiliently manually depressable to a suction applied closed position wherein said vent hole is obstructed to a closed to atmosphere position to seal off the passage to directly apply suction to the flexible tube, said stem body wall being cylindrical and said cap including an inwardly extending tubular plunger having an outer cylindrical wall movable inwardly and outwardly within said body wall from the normally open to atmosphere position where said plunger wall is disposed outwardly of said vent hole to a closed to atmosphere position where said plunger wall extends at least portions of said vent hole, said plunger terminating at its inner end in an annular surface having sealing means included thereon, said stem body wall including an annular ledge positioned inwardly of said vent hole, and said plunger annular sealing surface engaging said ledge in said closed to atmosphere position.

6. A normally open to atmosphere suction control regulator, said regulator having a main body with a suction lumen extending therethrough and in turn terminating at one end thereof in an entrance port and at the other end with a connector for applying suction to said lumen and a bypass stem having a stem body wall transversely extending outwardly from said main body and terminating in an open outer end having a peripheral rim and in turn including a vent passage which extends from said suction lumen outwardly to said open outer end, said entrance port, said suction lumen and said connector all open and unobstructed with no means therein for blocking passage of gases therethrough during operation of the regulator in either the non suction applying position or the suction applying position thereof, said stem body wall including at least one vent hole open to atmosphere and disposed at a point inwardly spaced from said outer end peripheral rim, a valve closure cap having a completely imperforate outer surface positioned on said outer end peripheral rim and closing said vent passage except for said vent hole, said cap outer surface of a lateral extent substantially greater than that of said stem body wall and overlaying said vent hole, said vent hole being shielded by said cap outer surface, said cap being normally biased to a non-suction applied open position wherein the vent hole remains open to atmosphere, and said being resiliently manually inwardly depressable to a suction applied closed position wherein said vent hole is obstructed to seal off the vent passage to a closed to atmosphere position.

7. A normally open to atmosphere suction control regulator, said regulator having a main body with a suction lumen extending therethrough and in turn terminating at one end thereof in an entrance port and at the other end with a connector for applying suction to said lumen and a bypass stem having a stem body wall transversely extending from said main body and terminating in an open outer end and in turn including a vent passage which extends from said suction lumen to said open outer end, said entrance port, said suction lumen and said connector all open and unobstructed with no means therein for blocking passage of gases therethrough during operation of the regulator in either the non suction applying position or the suction applying position thereof, said stem body wall including at least one vent hole open to atmosphere and disposed at a point inwardly spaced from said outer end, a completely closed valve closure cap positioned on said outer end and closing said vent passage except for said vent hole, said cap being normally biased to a non-suction applied open position wherein the vent hole remains open to atmosphere, and said cap being resiliently manually depressable to a suction applied closed position wherein said vent hole is obstructed to a closed to atmosphere position to seal off the passage to directly apply suction to the entrance port, said stem body wall being cylindrical and said cap including an inwardly extending tubular plunger having an outer cylindrical wall adapted to move inwardly and outwardly within said stem body wall from the normally open to atmosphere position where said plunger wall is disposed outwardly of said year hole to a closed to atmosphere position where said plunger wall extends across at least portions of said vent hole.

8. The catheter assembly of claim 7, said regulator main body being rigid and said closure cap being resilient.

9. The catheter assembly of claim 7, said valve closure cap having an outer upper surface wall hand engageable by the operator of the device and of a lateral extent substantially greater than that of said stem body wall, said vent hole being shielded by said upper surface.

10. A normally open to atmosphere suction control regulator, said regulator having a main body with a suction lumen extending therethrough and in turn terminating at one end thereof in an entrance port and at the other end with a connector for applying suction to said lumen and a bypass stem having a stem body wall transversely extending from said main body and terminating in an open outer end and in turn including a vent passage which extends from said suction lumen to said open outer end, said stem body wall including at least one vent hole open to atmosphere and disposed at a point inwardly spaced from said outer end, a completely closed valve closure cap positioned on said outer end so as to close said passageway except for said vent hole, said cap being normally biased to a non-suction applied open position wherein the vent hole remains open to atmosphere, and said cap being resiliently manually depressable to a suction applied closed position wherein said vent hole is obstructed to a closed to atmosphere position to seal of the passage to directly apply suction to the entrance port, said stem body wall being cylindrical and said cap including an inwardly extending tubular plunger having an outer cylindrical wall movable inwardly and outwardly within said stem body wall from the normally open to atmosphere position where said plunger wall is disposed outwardly of said vent hold to a closed to atmosphere position where said plunger wall extends across at least portions of said vent hole, said plunger terminating at its inner end in an annular surface having sealing means included thereon, said stem body wall including an annular ledge positioned inwardly of said vent hole, and said plunger annular sealing surface engaging said ledge in said closed to atmosphere position.

11. A medical aspirator comprising, a flexible catheter, a fluid flow regulator and a pliable envelope, said flexible catheter attached to and in fluid flow communication with said fluid flow regulator, said fluid flow regulator having a main-body portion with a side stem, said pliable-envelope having a distal end, a proximal end and a side wall connecting both said distal and proximal ends, with said proximal end of the pliable envelope including a hole perforating said side wall, said catheter and said regulator fully positioned within said pliable envelope with the side stem on said regulator passing through and sealingly engaging the proximally located walls of said hole on said pliable envelope and fixedly attaching said envelope to said catheter and regulator.

12. The aspirator of claim 11, wherein the catheter subassembly is visible through the pliable envelope.

13. The aspirator assembly of claim 12, wherein the pliable envelope includes an area of indicia greater than that of said hole and through which said hole is formed, a portion of said indicia surrounding said hole to visually mark and locate said hole.

14. A sterile suction catheter assembly normally open to atmosphere comprising a flexible tube and a suction control regulator in suction communication with each other, said regulator having a main body with a suction lumen extending therethrough and in turn terminating at one end thereof with said flexible tube and at the other end with a connector for applying suction to said assembly and a bypass stem having a stem body wall transversely extending from said main body and terminating in an open outer end and in turn including a vent passage which extends from said suction lumen to said open outer end, said flexible tube, said suction lumen and said connector all open and unobstructed with no means therein for blocking passage of gases therethrough during operation of the catheter assembly in either the non suction position or the suction applying position thereof, said stem body wall including at least one vent hole open to atmosphere and disposed at a point inwardly spaced from said outer end, a completely closed valve closure cap positioned on said outer end and closing said passageway except for said vent hole, said cap being normally biased to a non-suction applied open position wherein the vent hole remains open to atmosphere, and said cap being resiliently manually depressable to a suction applied closed position wherein said vent hole is obstructed to a closed to atmosphere position to seal off the passage to directly apply suction to the flexible tube, including a pliable envelope, said flexible tube attached to and in fluid flow communication with said suction control regulator, said pliable envelope having a distal end, a proximal end and a side wall connecting both said distal and proximal ends, with said proximal end of the pliable envelope including a hole perforating said side wall, said sterile suction catheter assembly including said regulator fully positioned within said pliable envelope with the side stem on said regulator passing through and sealingly engaging proximally located walls of said hole on said pliable envelope and fixedly attaching said envelope to said sterile suction catheter assembly and regulator.

15. A normally open to atmosphere suction control regulator, said regulator having a main body with a suction lumen extending therethrough and in turn terminating at one end thereof in an entrance port and at the other end with a connector for applying suction to said lumen and a bypass stem having a stem body wall transversely extending from said main body and terminating in an open outer end and in turn including a vent passage which extends from said suction lumen to said open outer end, said entrance port, said suction lumen and said connector all open and unobstructed with no means therein for blocking passage of gases therethrough during operation of the regulator in either the non suction applying position or the suction applying position thereof, said stem body wall including at least one vent hole open to atmosphere and disposed at a point inwardly spaced from said outer end, a completely closed valve closure cap positioned on said outer end and closing said vent passage except for said vent hole, said cap being normally biased to a non-suction applied open position wherein the vent hole remains open to atmosphere, and said cap being resiliently manually depressable to a suction applied closed position wherein said vent hole is obstructed to a close to atmosphere position to seal off the passage to directly apply suction to the entrance port, including a pliable envelope, said flexible tube attached to and in fluid flow communication with said suction control regulator, said pliable envelope having a distal end, a proximal end and a side wall connecting both said distal and proximal ends, with said proximal end of the pliable envelope including a hole perforating said side wall, said sterile suction catheter assembly including said regulator fully positioned within said pliable envelope with the side stem on said regulator passing through and sealingly engaging proximally located walls of said hole on said pliable envelope and fixedly attaching said envelope to said sterile suction catheter assembly and regulator.

* * * * *